Aug. 22, 1967 R. H. GAST Plant Pat. 2,762
HIBISCUS PLANT
Filed May 23, 1966
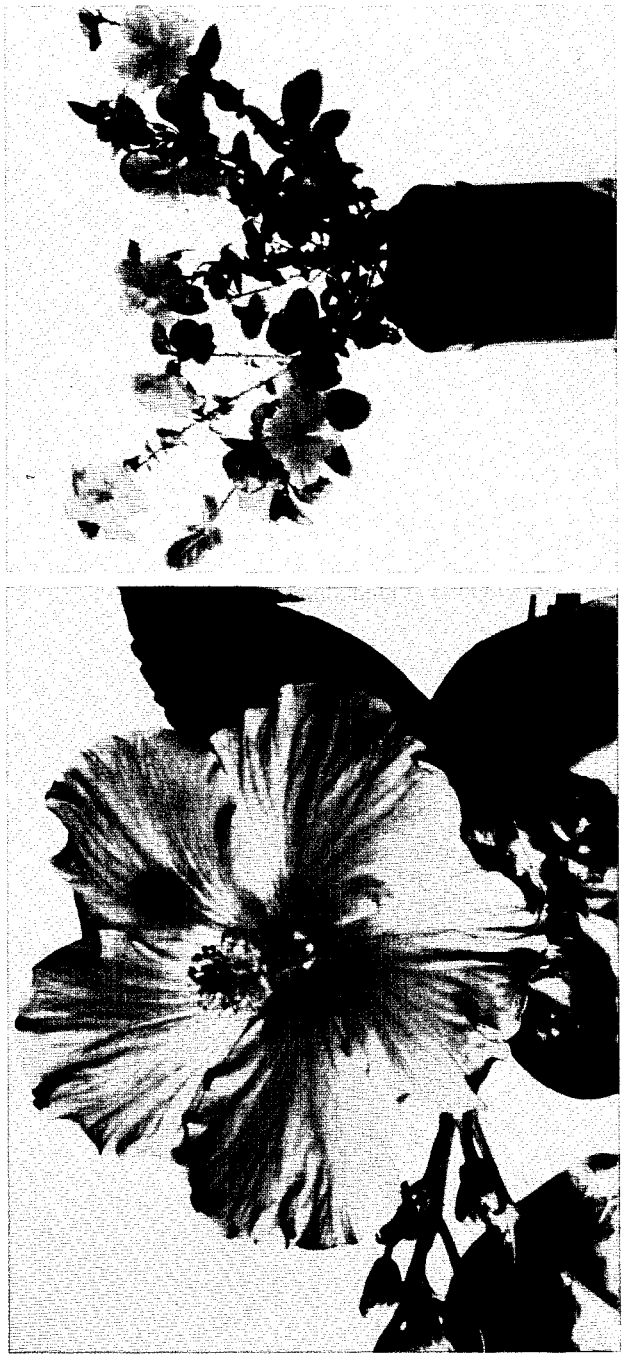
INVENTOR.
ROSS H. GAST,
By Edmond F. Shanahan.
ATTORNEY.

United States Patent Office

Plant Pat. 2,762
Patented Aug. 22, 1967

2,762
HIBISCUS PLANT

Ross H. Gast, Los Angeles, Calif., assignor to Monrovia Nursery Co., Azusa, Calif., a corporation of California Filed May 23, 1966, Ser. No. 552,354
1 Claim. (Cl. Plt.—54)

The present invention relates to a new and distinct variety of hibiscus plant, of the *Rosa-sinensis* species.

The plant is characterized as to novelty by its low-growing habit, the unique color arrangement of its brilliant flowers, and its large leaves.

This plant appeared as a seedling in 1959 after extensive breeding efforts. It is not similar to any known variety. The plant will not come true from seed; it can be truly reproduced only by asexual means, that is, grafting and cutting.

A plant and flower of the new variety are shown in full color in the accompanying illustration.

A detailed description of the new variety follows, and to facilitate identification of the important colors, the color terminology adopted by the British Horticultural Color Charts has been followed. (Reference is to "Horticultural Color Charts," issued by the British Color Council in two volumes, in collaboration with the Royal Horticultural Society, copyright by Robert F. Wilson, published 1938–41.)

*The plant*

Parentage: Seedling resulting from definite breeding efforts.

*Pollen parent.*—Barbara Buff.

*Seed parent.*—Hawaiian Agricultural Experiment Station #J11.

Growth: The plant is of moderate growth; its branches have a tendency to be spreading. The ultimate height of the plant is not known, but from observations made of plants which have been allowed to grow without being pruned or shaped, the plant will be about as broad as it is tall. Height should be from 4 to 4½ feet.

Branches: New branch growth is a light green, changing to a light greyish-brown as it matures. Bark is slightly rough.

Growth habit: Branching begins just above the ground level and has a tendency to be spreading.

Foliage: The leaves are of good substance and glossy.

*Shape.*—The leaves are best described as being broadly ovate, with the margin slightly undulate and coarsely-toothed. The apex of the leaf is more or less acuminate; the base truncate or obtuse.

*Color.*—The upper surface of the leaf is o960/1 Spinach Green, while the underside is Scheeles Green 860/1.

*Size.*—Leaves are from 2¼ to 3½ inches in width, and from 3¼ to 5 inches in length. Average length of the petiole is 1 inch.

*Arrangement.*—Leaves are alternate on the stems.

*Veins.*—Veins are prominent on the underside of the leaf, extending from the base of the leaf in a palmate fashion. Veins are slightly darker in color than the upper or undersides of the leaf.

*The flower*

The plant blooms in great abundance from May through October in southern California, with lighter bloom in April and November.

Form: Flowers are saucer-shaped, with the outer edge reflexed. Flowers vary from 5 to 6 inches in width.

Petals: Petals are five in number. They overlap and are slightly ruffled at the tips.

Color: The basic color of the petals is Fire Red 15/1. This color shows most prominently at the edge of the petals. There is a haze or overcast of Tyrian Rose 24 over the center of the petals, shading out to Fire Red 15/1 at the edge of the petals. The base of the petals is Tyrian Rose 24. The back of the petals is one-third Fawn Brown, with the balance being Delft Rose o20/1.

Veins: Veins of the petals on upperside of each petal are Tyrian Rose 24. Veins shade to Fire Red 15/1 at the edge of the petal.

Stigma pads: Stigma pads are Rose Red 724.

Style: Style is Tyrian Rose 24/2. The length of the style is 2¼ inches.

I claim:

A new and distinct variety of hibiscus plant, of *Rosa-sinensis* species, substantially as herein described and illustrated, and characterized particularly as to novelty by its low-growing habit, the unique color arrangement of its brilliant flowers, and its large leaves.

No references cited.

ABRAHAM G. STONE, *Primary Examiner.*

ROBERT E. BAGWILL, *Examiner.*